United States Patent [19]

Seno et al.

[11] 4,440,857
[45] Apr. 3, 1984

[54] PROCESS FOR PREPARING MYCAROSYLTYLACTONE

[75] Inventors: Eugene T. Seno, Norwich, England; Richard H. Baltz, Indianapolis, Ind.

[73] Assignee: Eli Lilly and Company, Indianapolis, Ind.

[21] Appl. No.: 359,385

[22] Filed: Mar. 18, 1982

Related U.S. Application Data

[63] Continuation of Ser. No. 173,313, Jul. 29, 1980, abandoned.

[51] Int. Cl.³ .................. C12P 17/16; C12P 17/08; C12R 1/54
[52] U.S. Cl. .................. 435/118; 435/124; 435/896
[58] Field of Search .................. 435/76, 118, 124

[56] References Cited

U.S. PATENT DOCUMENTS

| | | | |
|---|---|---|---|
| 3,178,341 | 4/1965 | Hamill et al. | 435/76 |
| 3,326,759 | 6/1967 | Hamill et al. | 167/65 |
| 3,344,024 | 9/1967 | Whaley et al. | 167/65 |
| 3,459,853 | 8/1969 | Gorman et al. | 424/121 |
| 3,684,794 | 8/1972 | Martin | 435/118 |
| 4,161,523 | 7/1979 | Weinstein et al. | 424/181 |
| 4,196,280 | 4/1980 | Umezawa et al. | 536/17 |

OTHER PUBLICATIONS

Lamanna et al., *Basic Bacteriology*, The William & Wilkins Co., pp. 723-727, (1965).
Metzler, *Biochemistry*, Academic Press, Inc., pp. 945-946, (1977).
Masamune et al., *J. Amer. Chem. Soc.*, 98, (24), 7874-7875, (1976).
Kinumaki et al., *J. Antibiotics*, 30, (6), 450-454, (1977).
Derwent Abstract 86252X/46 of Japanese Patent 6037-351, (Tanabe Pharm.).
Yamaguchi et al., *J. Antibiotics*, 31, (5), 433-440, (1978).
Derwent Abstract 86253X/46 of Japanese Patent 6037-352, (Tanabe Pharm.).
Tsukiura et al., *J. Antibiotics*, 22, (3), 89-99, (1969).
Suzuki et al., *Chemistry Letters*, 1973, 793-798.
Nash et al., Current Chemother. & Infect. Diseases Proceedings of 11th ICC & 19th ICAAC, *American Society of Microbiology*, 1980, pp. 462-463.
Nagel et al., *J. Org. Chem.*, 44, (12), 2050-2052, (1979).
Grafe et al., *J. Antibiotics*, 33, (6), 663-664, and 574-578, (1980).
Omura et al., Abstract, "A Study on 16-Membered Macrolides (Pt. 32)", Proceedings of 100th Meeting of the Pharmaceutical Soc. Japan, Mar. 10, 1980, (translation by Omura).
Baltz et al., "Properties of Streptomyces fradiae Mutants Blocked in Biosynthesis of the Macrolide Antibiotic Tylosin", *Antimicrobial Agents and Chemotherapy*, vol. 20, No. 2, Aug. 1981, pp. 214-225.

*Primary Examiner*—Alvin E. Tanenholtz
*Attorney, Agent, or Firm*—Nancy J. Harrison; Arthur R. Whale

[57] ABSTRACT

A new microorganism, Streptomyces fradiae NRRL 12201, which produces mycarosyltylactone (5-O-mycarosyl-20-dihydro-20,23-dideoxytylonolide) and a process for preparing tylactone (20-dihydro-20,23-dideoxytylonolide) and mycarosyltylactone by submerged aerobic fermentation of this microorganism, or a mycarosyltylactone-producing mutant or recombinant thereof, are provided.

6 Claims, 1 Drawing Figure

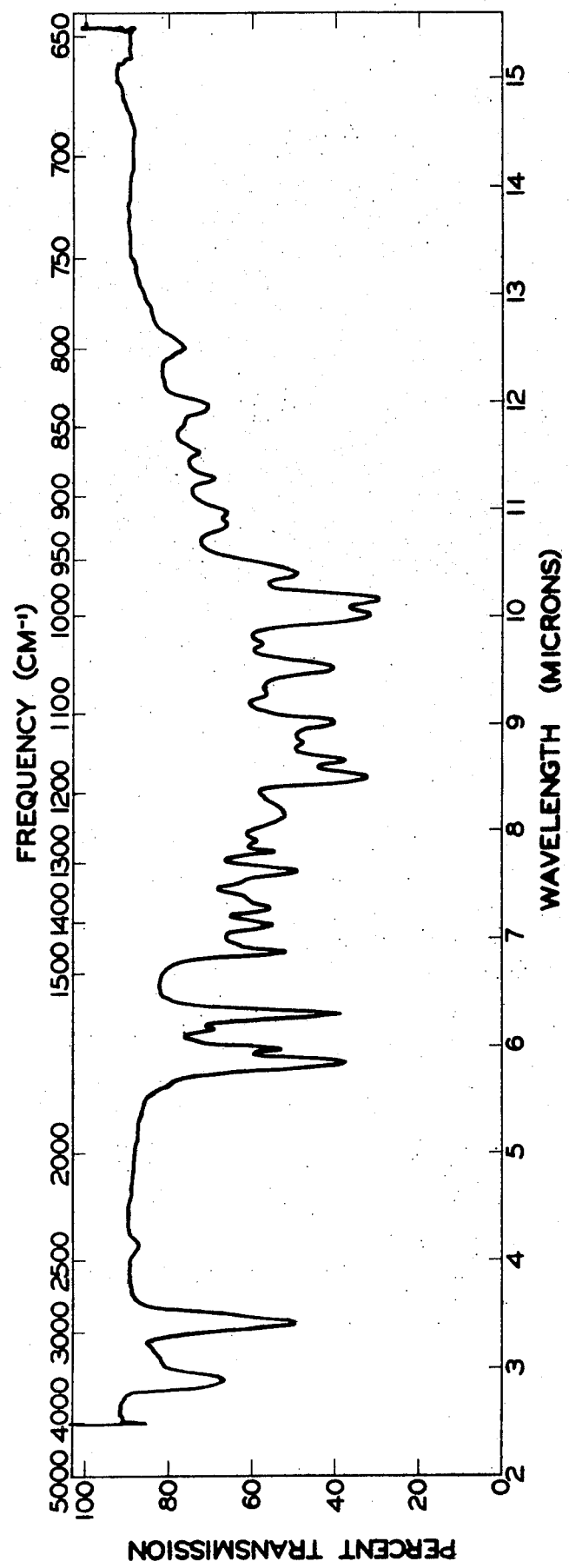

PROCESS FOR PREPARING MYCAROSYLTYLACTONE

This application is a continuation of application Ser. No. 173,313, filed July 29, 1980 now abandoned.

SUMMARY OF THE INVENTION

This invention relates to a new strain of *Streptomyces fradiae* and to a process for preparing tylactone and a new macrolide compound by submerged aerobic fermentation of this new strain. The new compound, which is 5-O-mycarosyl-20-dihydro-20,23-dideoxytylonolide, will be called mycarosyltylactone for convenience herein. Mycarosyltylactone has structure 1:

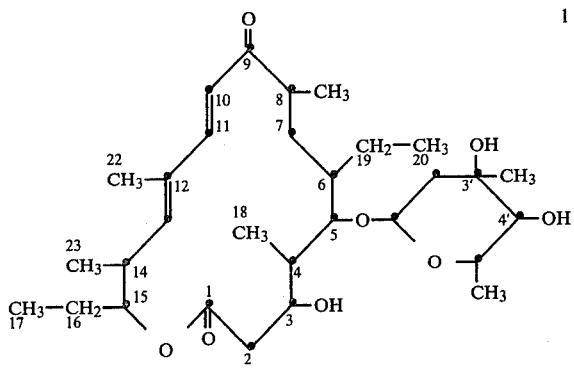

Mycarosyltylactone is disclosed in a co-pending patent application by Robert L. Hamill and Gene M. Wild entitled MYCAROSYLTYLACTONE, U.S. Ser. No. 173,312, filed July 29, 1980 now U.S. Pat. No. 4,299,953, issued Nov. 10, 1981.

Tylactone has structure 2:

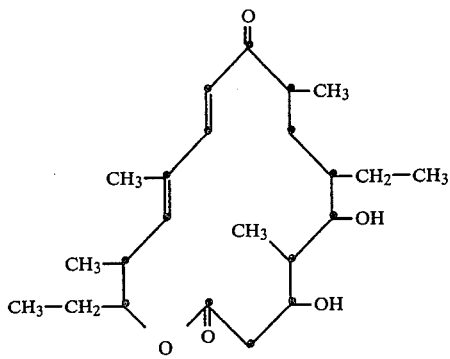

Tylactone is the subject of a co-pending patent application of Robert L. Hamill, Gerald L. Huff, Richard H. Baltz and Eugene T. Seno, entitled TYLACTONE, Ser. No. 162,976 filed July 2, 1980. Another method for making tylactone is the subject of our co-pending patent application entitled PROCESS FOR PREPARING TYLACTONE, Ser. No. 162,977, filed July 2, 1980.

Tylactone and mycarosyltylactone are useful intermediates from which 16-membered macrolide antibiotics can be prepared. Although no stereochemical assignments are indicated in the structures given herein, the stereochemistry of the compounds is identical to that of the corresponding portion of tylosin.

DESCRIPTION OF THE DRAWING

The infrared absorption spectrum of mycarosyltylactone in chloroform is presented in the accompanying drawing.

DETAILED DESCRIPTION

This invention relates to a new microorganism and to a new process which uses this microorganism. The new microorganism is a mutant strain of *Streptomyces fradiae*. The new process is a method of making mycarosyltylactone and tylactone by fermentation of this *Streptomyces fradiae* strain under submerged aerobic conditions until a substantial amount of these compounds are produced.

The following paragraphs describe the properties of mycarosyltylactone, the new macrolide compound produced by the process of this invention.

Mycarosyltylactone

The structure of mycarosyltylactone is shown in formula 1. Mycarosyltylactone is a white solid which crystallizes from heptane, hexane or ethyl acetate-hexane and which melts at about 182°–184° C. It has the following approximate percentage elemental composition: carbon, 67%; hydrogen, 9%; and oxygen, 24%. It has an empirical formula of $C_{30}H_{50}O_8$ and a molecular weight of about 538.

The infrared absorption spectrum of mycarosyltylactone in chloroform is shown in the accompanying drawing. Observable absorption maxima occur at the following frequencies ($cm^{-1}$): 3640 (medium), 2941 and 2907 [doublet (strong)], 2421 (very small), 1712 (strong), 1678 (medium), 1623 (small), 1590 (strong), 1456 (medium), 1404 (small), 1374 (small), 1359 (shoulder), 1314 (small), 1284 (small), 1263 (very small), 1229 (small), 1178 (strong), 1157 (medium), 1134 (very small), 1109 (small), 1078 (very small), 1050 (medium), 1025 (very small), 1000 (strong), 984 (strong), 962 (medium), 920 (very small), 911 (very small), 887 (small), 867 (small), 848 (shoulder), 836 (small), and 799 (small).

The ultraviolet absorption spectrum of mycarosyltylactone in neutral ethanol exhibits an absorption maximum at about 282 nm ($E_{1\ cm}^{1\%} = 568$).

Mycarosyltylactone is nearly insoluble in water, but is soluble in organic solvents such as acetone, methanol, ethanol, dimethylformamide, chloroform, diethyl ether, petroleum ether, benzene and dimethyl sulfoxide.

One important use of mycarosyltylactone is as an intermediate to make tylactone and tylactone derivatives. The following paragraphs describe the properties of tylactone.

Tylactone

The structure of tylactone is shown in formula 2. Tylactone is a white solid which crystallizes from heptane, hexane or ethyl acetate-hexane and which melts at about 162°–163° C. It has the following approximate percentage elemental composition: carbon, 70%; hydrogen, 9.7%; oxygen, 20.3%. It has an empirical formula of $C_{23}H_{38}O_5$ and a molecular weight of about 394.

The infrared absorption spectrum of tylactone in chloroform has observable absorption maxima at the following frequencies ($cm^{-1}$): 3534 (medium), 2924 (strong), 2398 (weak), 2353 (weak), 1709 (very strong), 1678 (very strong), 1626 (small), 1592 (very strong), 1458 (strong), 1441 (shoulder), 1404 (strong), 1379 (small), 1316 (strong), 1284 (medium), 1181 (very strong), 1143 (strong), 1103 (medium), 1078 (medium), 1049 (very small), 1025 (medium), 984 (very strong), 958 (strong), 923 (medium), 911 (shoulder), 859 (small), 868 (medium), 840 (medium), 820 (very small) and 661 (small).

The ultraviolet (UV) absorption spectrum of tylactone in neutral ethanol exhibits an absorption maximum at about 282 nm ($E_1\ _{cm}^{1\%} = 560$).

Tylactone has the following specific rotation:
$[\alpha]_D^{25} - 55.23°$ (c 1, $CH_3OH$).

Electrometric titration of tylactone in 66% aqueous dimethylformamide indicates it has no titratable groups.

Tylactone is nearly insoluble in water, but is soluble in organic solvents such as acetone, methanol, ethanol, dimethylformamide, chloroform, diethyl ether, petroleum ether, benzene and dimethyl sulfoxide.

Chromatography of Mycarosyltylactone

Mycarosyltylactone can be distinguished from tylactone and tylosin by silica-gel thin-layer chromatography (TLC). Sulfuric acid spray, either concentrated or diluted (50%), may be used for detection. With this detection system tylactone appears initially as a yellow-to-brown spot, and mycarosyltylactone appears as a blue-purple spot. If silica-gel plates with a fluorescent background are used in the chromatography, UV detection is convenient. The approximate Rf values of mycarosyltylactone are summarized in Table 1.

TABLE 1

TLC of Mycarosyltylactone[a]

| Compound | Rf Value | |
|---|---|---|
| | A[b] | B |
| Mycarosyltylactone | 0.17 | 0.44 |
| Tylactone | 0.50 | 0.62 |
| Tylosin | 0.0 | 0.0 |

[a]Medium: Silica gel
[b]Solvent:
A = benzene:ethyl acetate (4:1)
B = benzene:ethyl acetate (3:2)

Preparation of Mycarosyltylactone and Tylactone

Mycarosyltylactone and tylactone are prepared by culturing a strain of Streptomyces fradiae which produces these compounds under submerged aerobic conditions in a suitable culture medium until a substantial amount of compound is produced.

The culture medium used to grow the Streptomyces fradiae can be any one of a number of media. For economy in production, optimal yield, and ease of product isolation, however, certain culture media are preferred. Thus, for example, preferred carbon sources in large-scale fermentation include carbohydrates such as dextrin, glucose, starch, and corn meal and oils such as soybean oil. Preferred nitrogen sources include corn meal, soybean meal, fish meal, amino acids and the like. Among the nutrient inorganic salts which can be incorporated in the culture media are the customary soluble salts capable of yielding iron, potassium, sodium, magnesium, calcium, ammonium, chloride, carbonate, sulfate, nitrate, and like ions.

Essential trace elements necessary for the growth and development of the organism should also be included in the culture medium. Such trace elements commonly occur as impurities in other constituents of the medium in amounts sufficient to meet the growth requirements of the organism. It may be necessary to add small amounts (i.e. 0.2 ml/L) of an antifoam agent such as polypropylene glycol (M.W. about 2000) to large-scale fermentation media if foaming becomes a problem.

As is customary in aerobic submerged culture processes, sterile air is bubbled through the culture medium. For efficient antibiotic production the percent of air saturation for tank production should be about 30% or above (at 28° C. and one atmosphere of pressure).

For production of substantial quantities of these compounds, submerged aerobic fermentation in tanks is preferred. Small quantities may be obtained by shake-flask culture. Because of the time lag in production commonly associated with inoculation of large tanks with the spore form of the organism, it is preferable to use a vegetative inoculum. The vegetative inoculum is prepared by inoculating a small volume of culture medium with the spore form or mycelial fragments of the organism to obtain a fresh, actively growing culture. The vegetative inoculum is then transferred to a larger tank. The medium used for the vegetative inoculum can be the same as that used for larger fermentations, but other media can also be used.

Production of mycarosyltylactone and tylactone can be followed during the fermentation by testing samples of the broth, using TLC or high-performance liquid chromatography with a UV detection system.

Following their production under submerged aerobic fermentation conditions, mycarosyltylactone or tylactone can be recovered from the fermentation medium by methods used in the fermentation art. Because of the limited solubility of these compounds in water, they may not be altogether soluble in the medium in which they are produced. Recovery can be accomplished by (1) extraction of the fermentation broth or (2) filtration of the fermentation broth and extraction of both the filtered broth and the mycelial cake. A variety of techniques may be used in the extraction processes. A preferred technique for purification of the filtered broth involves extracting the broth (generally without pH adjustment) with a suitable solvent such as amyl acetate or petroleum ether, concentrating the organic phase under vacuum to give crystals or an oil. The crystals or oil thus obtained may be purified by adsorption chromatography to give mycarosyltylactone and tylactone.

The Microorganism

The new microorganism of this invention was obtained by chemical mutagenesis of a Streptomyces fradiae strain which produces tylosin. The new microorganism produces only minimal amounts of tylosin, but produces mycarosyltylactone and tylactone as major components. The new microorganism is also classified as a strain of Streptomyces fradiae. A culture of this microorganism has been deposited and made part of the stock culture collection of the Northern Regional Research Center, Agricultural Research, North Central Region, 1815 North University St., Peoria, Ill., 61604, from which it is available to the public under the accession number NRRL 12201.

As is the case with other organisms, the characteristics of Streptomyces fradiae NRRL 12201 are subject to variation. Recombinants, mutants or variants of the NRRL 12201 strain may be obtained by methods known in the art. For example, mutants can be obtained by treatment with various known physical and chemical mutagens, such as ultraviolet light, X-rays, gamma rays, and N-methyl-N'-nitro-N-nitrosoguanidine. All natural and induced variants, mutants and recombinants of Streptomyces fradiae NRRL 12201 which retain the characteristic of mycarosyltylactone production are a part of this invention.

*S. fradiae* NRRL 12201 can be grown at temperatures between about 10° and about 40° C. Optimum production of mycarosyltylactone appears to occur at temperatures of about 28° C.

Tylactone and mycarosyltylactone are useful intermediates from which 16-membered macrolide antibiotics can be prepared. Mycarosyltylactone (1) can be hydrolyzed using mild acid conditions to give tylactone (2). Mild acid hydrolysis conditions are known in the art. Appropriate solutions having a pH of about four or below can be used to accomplish the hydrolysis. A polar organic cosolvent, such as an alcohol (for example, ethanol) should be included to keep the reactants in solution. Temperatures of about 20° to about 100° C. can be used in this method. The reaction time needed to carry out the hydrolysis varies, depending upon the pH of the reaction mixture and the temperature used. At higher pH levels the reaction rate is slower, and at higher temperatures the reaction rate is faster. The reaction is carried out by treating mycarosyltylactone with a mild acid solution for a time sufficient to effect removal of the mycarosyl group to give tylactone.

Alternatively, and sometimes preferably, tylactone can be prepared by treating mycarosyltylactone in the fermentation broth in which it is produced, using mild acidic conditions as above described for a time sufficient to convert the mycarosyltylactone to tylactone. Tylactone thus prepared can be isolated from the fermentation broth using techniques known in the art.

Tylactone can be bioconverted to tylosin or tylosin-related compounds as described by Hamill et al. in Ser. No. 162,976. The bioconversion is accomplished by adding tylosin to a growing culture of a bioconverting microorganism. The bioconverting microorganism can be a Streptomyces strain which either produces tylosin itself or is capable of producing tylosin except that it is blocked in tylactone formation.

A strain which is capable of producing tylosin except that it is blocked in tylactone formation can be obtained by treating a tylosin-producing strain with a mutagen and screening survivors for those which are unable to produce tylosin. Those survivors which are unable to produce tylosin are further screened to determine which strains are unable to produce tylactone but are still capable of bioconverting tylactone to tylosin. These strains are identified by adding tylactone to small shake-flask cultures of the selected survivors to determine if they bioconvert tylactone to tylosin.

*Streptomyces fradiae* strains NRRL 2702 and NRRL 2703 are examples of Streptomyces strains which are capable of producing tylosin. A typical mutagen which may be used to obtain the selected strains is N-methyl-N'-nitro-N-nitrosoguanidine.

Tylactone is especially useful in the preparation of labeled compounds for biosynthetic or metabolic studies. By labeling either the tylactone portion or the added sugar moieties, specifically labeled tylosin useful for biosynthetic or metabolic studies can be obtained.

In order to illustrate more fully the operation of this invention, the following examples are provided:

EXAMPLE 1

A. Shake-flask Fermentation of Mycarosyltylactone and Tylactone

A lyophilized pellet of *Streptomyces fradiae* NRRL 12201 is dispersed in 1-2 ml of sterilized water. A portion of this solution (0.5 ml) is used to inoculate a vegetative medium (150 ml) having the following composition:

| Ingredient | Amount (%) |
| --- | --- |
| Corn steep liquor | 1.0 |
| Yeast extract | 0.5 |
| Soybean grits | 0.5 |
| CaCO$_3$ | 0.3 |
| Soybean oil (crude) | 0.45 |
| Deionized water | 97.25 |

Alternatively, a vegetative culture of *S. fradiae* NRRL 12201 preserved, in 1-ml volumes, in liquid nitrogen is rapidly thawed and used to inoculate the vegetative medium. The inoculated vegetative medium is incubated in a 500-ml Erlenmeyer flask at 29° C. for about 48 hours on a closed-box shaker at about 300 rpm.

This incubated vegetative medium (0.5 ml) is used to inoculate 7 ml of a production medium having the following composition:

| Ingredient | Amount (%) |
| --- | --- |
| Beet molasses | 2.0 |
| Corn meal | 1.5 |
| Fish meal | 0.9 |
| Corn gluten | 0.9 |
| NaCl | 0.1 |
| (NH$_4$)$_2$HPO$_4$ | 0.04 |
| CaCO$_3$ | 0.2 |
| Soybean oil (crude) | 3.0 |
| Deionized water | 91.36 |

The inoculated fermentation medium is incubated in a 50-ml bottle at 29° C. for about 6 days on a closed-box shaker at 300 rpm.

B. Tank Fermentation of Mycarosyltylactone and Tylactone

In order to provide a larger volume of inoculum, 60 ml of vegetative culture prepared in a manner similar to that described in section A, is used to inoculate 38 L of a second-stage vegetative growth medium having the following composition:

| Ingredient | Amount (%) |
| --- | --- |
| Corn steep liquor | 1.0 |
| Soybean meal | 0.5 |
| Yeast extract | 0.5 |
| CaCO$_3$ | 0.3 |
| Soybean oil (crude) | 0.5 |
| Lecithin (crude) | 0.015 |
| Water | 97.185 |
| Adjust pH to 8.5 with 50% NaOH solution. | |

This second-stage vegetative medium is incubated in a 68-liter tank for about 47 hours at 29° C.

Second-stage culture (4 L) thus prepared is used to inoculate 40 liters of sterile production medium having the following composition:

| Ingredient | Amount (%) |
| --- | --- |
| Fish meal | 0.92 |
| Corn meal | 1.57 |
| Corn gluten | 0.92 |
| CaCO$_3$ | 0.21 |
| NaCl | 0.10 |
| (NH$_4$)$_2$HPO$_4$ | 0.04 |

| Ingredient | Amount (%) |
| --- | --- |
| Beet molasses | 2.10 |
| Soybean oil (crude) | 3.15 |
| Lecithin | 0.09 |
| Water | 90.90 |
| Adjust pH to 7.2 with 50% NaOH solution. | |

The inoculated production medium is allowed to ferment in a 68-liter tank for about 5 days at a temperature of 28° C. The fermentation medium is aerated with sterile air to keep the dissolved oxygen level between about 30% and 50% and is stirred with conventional agitators at about 300 rpm.

EXAMPLE 2

Isolation of Mycarosyltylactone and Tylactone

Fermentation broth (900 ml), obtained as described in Example 1, Section A, is extracted with petroleum ether (900 ml). The petroleum ether extract is concentrated under an air stream to give an oil. The oil is dissolved in a small amount of ethyl acetate (about 15 ml). Heptane (about 15-20 ml) is added. The ethyl acetate is slowly allowed to evaporate to permit crystallization. The crystals are separated to give 450 mg of a crystalline mixture of tylactone and mycarosyltylactone.

Additional material can be obtained by adding an equal volume of methanol to the remaining whole broth, filtering the resulting solution, and extracting the filtrate with methylene chloride.

The crystalline mixture (400 mg) is separated by dissolving it in benzene. The benzene solution is chromatographed over a silica-gel (Woelm) column, packed with benzene. Elution is monitored by silica-gel thin-layer chromatography, using a benzene:ethyl acetate (3:2) solvent system and conc. sulfuric acid spray for detection. The column is first eluted with benzene to remove lipid substances, then with one liter of benzene:ethyl acetate (9:1), 1400 ml of benzene:ethyl acetate (6:1) and 900 ml of benzene:ethyl acetate (3:1) to separate and isolate tylactone and mycarosyltylactone. Fractions having a volume of about 150 ml are collected. Tylactone is eluted first (fractions 14-19), and mycarosyltylactone is eluted later (fractions 22-26). Fractions containing each are combined, evaporated under vacuum, and crystallized from heptane to give 160 mg of tylactone and 120 mg of mycarosyltylactone.

EXAMPLE 3

Preparation of Tylactone from Mycarosyltylactone

Mycarosyltylactone, prepared as described in Example 2, is dissolved in a methanol-aqueous hydrochloric acid solution (pH 1.8). The resulting solution is allowed to stand until hydrolysis is complete (about 48 hours) at room temperature and then is adjusted to pH 7.0 by the addition of sodium hydroxide. This solution is extracted with ethyl acetate, dichloromethane or chloroform. The extract is dried under vacuum to give tylactone.

EXAMPLE 4

Alternate Preparation of Tylactone from Mycarosyltylactone

Mycarosyltylactone, prepared as described in Example 1, is treated using the procedure of Example 3 to give tylactone in the fermentation broth. The tylactone is isolated according to the procedure of Example 2.

EXAMPLE 5

Preparation of Tylosin from Tylactone

A *Streptomyces fradiae* strain which formerly produced tylosin but which is blocked in macrolide ring closure is fermented according to the procedure described in Example 1, Section A. A temperature of 28° C. is used. Tylactone is added to the fermentation 48 hours after inoculation. The fermentation is then continued until a substantial amount of tylosin is produced, i.e. about three additional days. The presence of tylosin is determined by testing samples of the broth against organisms known to be sensitive to tylosin. One useful assay organism is *Staphylococcus aureus* ATCC 9144. Bioassay is conveniently performed by an automated turbidometric method. Alternative assay methods include thin-layer chromatography and high-performance liquid chromatography with UV detection.

EXAMPLE 6

Preparation of Labeled Tylosin

Mycarosyltylactone is prepared by the method of Examples 1 and 2 except that a labeled acetate, propionate, or butyrate is incorporated into the fermentation medium. Labeled mycarosyltylactone thus produced is used to prepare labeled tylactone by the method of Example 3. Using the procedure of Example 5 the labeled tylactone is converted to tylosin which is labeled on the macrolide ring.

EXAMPLE 7

Alternate Preparation of Labeled Tylosin

Tylactone, prepared by the method of Example 3, is used to prepare tylosin according to the method of Example 5 except that a labeled sugar moiety such as glucose is added to the second fermentation to provide tylosin which is labeled on the sugar moieties.

We claim:

1. A process for preparing the compound mycarosyltylactone, which has the formula

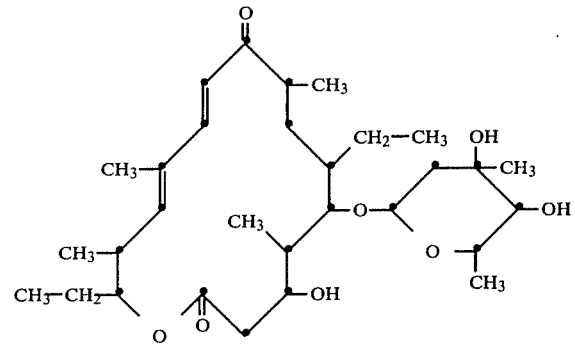

which comprises cultivating *Streptomyces fradiae* NRRL 12201 or a mycarosyltylactone-producing mutant or recombinant thereof in a culture medium containing assimilable sources of carbon, nitrogen, and inorganic salts under submerged aerobic fermentation conditions until a substantial amount of compound is produced and isolating the mycarosyltylactone.

2. The method of claim 1 which comprises cultivating *Streptomyces fradiae* NRRL 12201.

3. A process for preparing tylactone, which has the formula:

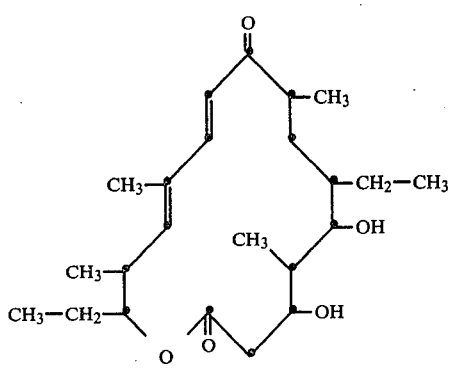

which comprises cultivating *Streptomyces fradiae* NRRL 12201 in a culture medium containing assimilable sources of carbon, nitrogen, and inorganic salts under submerged aerobic fermentation conditions until a substantial amount of tylactone is produced and isolating the tylactone.

4. A process for preparing tylactone which comprises cultivating *Streptomyces fradiae* NRRL 12201 in a culture medium containing assimilable sources of carbon, nitrogen, and inorganic salts under submerged aerobic fermentation conditions until a substantial amount of mycarosyltylactone is produced, treating the fermentation broth with mild acidic conditions to convert the mycarosyltylactone to tylactone, and isolating the tylactone.

5. The biologically purified culture of microorganism *Streptomyces fradiae* NRRL 12201 or a mycarosyltylactone-producing mutant or recombinant thereof.

6. The microorganism of claim 5 which is *Streptomyces fradiae* NRRL 12201.

* * * * *